(12) United States Patent
Orszulak et al.

(10) Patent No.: US 7,282,049 B2
(45) Date of Patent: Oct. 16, 2007

(54) ELECTROSURGICAL SYSTEM EMPLOYING MULTIPLE ELECTRODES AND METHOD THEREOF

(75) Inventors: James H. Orszulak, Nederland, CO (US); James W. McPherson, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 11/242,217

(22) Filed: Oct. 3, 2005

(65) Prior Publication Data

US 2006/0079886 A1 Apr. 13, 2006

Related U.S. Application Data

(60) Provisional application No. 60/616,967, filed on Oct. 8, 2004.

(51) Int. Cl.
A61B 18/18 (2006.01)

(52) U.S. Cl. .......................... 606/34; 606/42

(58) Field of Classification Search ................ 607/115, 607/116, 100–102, 122; 606/32–42, 45–50
See application file for complete search history.

(56) References Cited

U.S. PATENT DOCUMENTS

| | | | |
|---|---|---|---|
| 4,074,718 A | 2/1978 | Morrison, Jr. et al. |
| 4,411,266 A | 10/1983 | Cosman |
| 4,565,200 A | 1/1986 | Cosman |
| 4,576,177 A | 3/1986 | Webster, Jr. |
| 4,608,977 A | 9/1986 | Brown |
| 4,662,383 A | 5/1987 | Sogawa et al. |
| 4,739,759 A | 4/1988 | Rexroth et al. |
| 4,832,024 A | 5/1989 | Boussignac et al. |
| 4,880,719 A | 11/1989 | Murofushi et al. |
| 4,961,435 A | 10/1990 | Kitagawa et al. |
| 4,966,597 A | 10/1990 | Cosman |
| 4,993,430 A | 2/1991 | Shimoyama et al. |
| 5,029,588 A | 7/1991 | Yock et al. |
| 5,103,804 A | 4/1992 | Abele et al. |

(Continued)

FOREIGN PATENT DOCUMENTS

DE      2407559      2/1974

(Continued)

OTHER PUBLICATIONS

European Search Report from Application EP 05021935, 2006.

(Continued)

*Primary Examiner*—Michael Peffley (57) ABSTRACT

A system for heat ablation of tissue in a patient comprises a plurality of electrodes operatively connected to a source of radiofrequency energy and configured to apply RF energy to tissue at a patient site, a plurality of RF current restricting circuits, each circuit coupled between one of the plurality of electrodes and the source of radiofrequency energy, and configured to restrict RF energy to the electrode when the current restricting circuit is enabled and not restrict RF energy to flow to the electrode when the current restricting circuit is disabled, at least one return electrode adapted to contact the patient and configured to return RF energy to the RF source; and a switching mechanism configured to selectively enable each of the plurality of RF current restricting circuits, in one of a sequential and non sequential fashion, wherein the switching mechanism is isolated from each of the current restricting circuits.

18 Claims, 9 Drawing Sheets

U.S. PATENT DOCUMENTS

| | | |
|---|---|---|
| 5,225,741 A | 7/1993 | Auld, Jr. et al. |
| 5,230,623 A | 7/1993 | Guthrie et al. |
| 5,233,515 A | 8/1993 | Cosman |
| 5,246,438 A | 9/1993 | Langberg |
| 5,267,994 A | 12/1993 | Gentelia et al. |
| 5,281,213 A | 1/1994 | Milder et al. |
| 5,323,778 A | 6/1994 | Kandarpa et al. |
| 5,330,518 A | 7/1994 | Nielson et al. |
| 5,334,193 A | 8/1994 | Nardella |
| 5,342,357 A | 8/1994 | Nardella |
| 5,348,554 A | 9/1994 | Imran et al. |
| 5,370,675 A | 12/1994 | Edwards et al. |
| 5,383,876 A | 1/1995 | Nardella |
| 5,383,917 A | 1/1995 | Desai et al. |
| 5,385,148 A | 1/1995 | Lesh et al. |
| 5,403,311 A | 4/1995 | Abele et al. |
| 5,409,000 A | 4/1995 | Imran |
| 5,409,006 A | 4/1995 | Buchholtz et al. |
| 5,433,739 A | 7/1995 | Sluijter et al. |
| 5,458,597 A | 10/1995 | Edwards et al. |
| 5,462,521 A | 10/1995 | Brucker et al. |
| 5,472,441 A | 12/1995 | Edwards et al. |
| 5,490,850 A | 2/1996 | Ellman et al. |
| 5,500,012 A | 3/1996 | Brucker et al. |
| 5,520,684 A | 5/1996 | Imran |
| 5,536,267 A | 7/1996 | Edwards et al. |
| 5,571,147 A | 11/1996 | Sluijter et al. |
| 5,588,432 A | 12/1996 | Crowley |
| 5,599,345 A | 2/1997 | Edwards et al. |
| 5,643,197 A | 7/1997 | Brucker et al. |
| 5,647,871 A | 7/1997 | Levine et al. |
| 5,662,111 A | 9/1997 | Cosman |
| 5,688,267 A | 11/1997 | Panescu et al. |
| 5,735,847 A | 4/1998 | Gough et al. |
| 5,775,338 A | 7/1998 | Hastings |
| 5,792,146 A | 8/1998 | Cosman |
| 5,848,967 A | 12/1998 | Cosman |
| 5,849,011 A | 12/1998 | Jones et al. |
| 5,868,740 A | 2/1999 | LeVeen et al. |
| 5,921,982 A | 7/1999 | Lesh et al. |
| 5,951,546 A | 9/1999 | Lorentzen |
| 6,001,093 A * | 12/1999 | Swanson et al. ............... 606/41 |
| 6,006,126 A | 12/1999 | Cosman |
| 6,053,912 A | 4/2000 | Panescu et al. |
| 6,059,780 A | 5/2000 | Gough et al. |
| 6,061,551 A * | 5/2000 | Sorrells et al. ............. 455/118 |
| 6,074,389 A | 6/2000 | Levine et al. |
| 6,080,149 A | 6/2000 | Huang et al. |
| 6,106,524 A | 8/2000 | Eggers et al. |
| 6,132,426 A | 10/2000 | Kroll |
| 6,146,380 A | 11/2000 | Racz et al. |
| 6,162,216 A | 12/2000 | Guziak et al. |
| 6,203,541 B1 | 3/2001 | Keppel |
| 6,241,725 B1 | 6/2001 | Cosman |
| 6,287,305 B1 | 9/2001 | Heim et al. |
| 6,306,132 B1 | 10/2001 | Moorman et al. |
| 6,337,998 B1 | 1/2002 | Behl et al. |
| 6,478,793 B1 | 11/2002 | Cosman et al. |
| 6,500,172 B1 | 12/2002 | Panescu et al. |
| 6,506,189 B1 | 1/2003 | Rittman, III et al. |
| 6,530,922 B2 | 3/2003 | Cosman et al. |
| 6,575,969 B1 | 6/2003 | Rittman, III et al. |
| 6,605,085 B1 | 8/2003 | Edwards |
| 2001/0034518 A1 | 10/2001 | Edwards et al. |
| 2002/0111615 A1 | 8/2002 | Cosman et al. |
| 2002/0120261 A1 | 8/2002 | Morris et al. |
| 2002/0156472 A1 | 10/2002 | Lee et al. |
| 2003/0018247 A1 | 1/2003 | Gonzalez |
| 2004/0002745 A1 | 1/2004 | Fleming et al. |
| 2004/0039429 A1 | 2/2004 | Daniel et al. |
| 2004/0181216 A1 | 9/2004 | Kelly et al. |
| 2004/0199161 A1 | 10/2004 | Truckai et al. |
| 2004/0254573 A1 | 12/2004 | Dycus |
| 2005/0107784 A1 | 5/2005 | Moses |
| 2005/0107785 A1 | 5/2005 | Dycus |
| 2005/0113824 A1 | 5/2005 | Sartor et al. |
| 2005/0119655 A1 | 6/2005 | Moses |
| 2005/0154387 A1 | 7/2005 | Moses |
| 2005/0155743 A1 | 7/2005 | Getz et al. |
| 2005/0192564 A1 | 9/2005 | Cosman et al. |
| 2006/0079885 A1 | 4/2006 | Rick et al. |
| 2006/0079886 A1 | 4/2006 | Orszulak |
| 2006/0079887 A1 * | 4/2006 | Buysse et al. ............... 606/41 |

FOREIGN PATENT DOCUMENTS

| | | |
|---|---|---|
| DE | 10224154 | 12/2003 |
| EP | 0171967 A | 2/1986 |
| EP | 0246350 | 11/1987 |
| EP | 0310431 | 4/1989 |
| EP | 0608609 | 8/1994 |
| EP | 1 070 518 A2 | 1/2001 |
| EP | 1465037 A | 10/2004 |
| FR | 2864439 | 7/2005 |
| WO | WO93/24066 | 12/1993 |
| WO | WO94/28809 | 12/1994 |
| WO | WO96/04860 | 2/1996 |
| WO | WO96/18349 | 6/1996 |
| WO | WO96/29946 | 10/1996 |
| WO | WO96/34571 | 11/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/17029 | 5/1997 |
| WO | WO99/01074 | 1/1999 |
| WO | WO99/04710 | 2/1999 |
| WO | WO99/22657 | 5/1999 |
| WO | WO 00/067846 | 11/2000 |
| WO | WO 01/00114 A1 | 1/2001 |
| WO | WO 2005/009528 | 2/2005 |

OTHER PUBLICATIONS

Cosman ER, Cosman BJ: "Methods of Making Nervous System Lesions", in William RH, Rengachary SS (eds): Neurosurgery. New York: McGraw-Hill, vol. 111, pp. 2490-2498, 1984.

Anderson, Gary et al., "A numerical study of rapid heating for high temperature radio frequency hyperthermia", International Journal of Bio-Medical Computing, 35 (1994) 297-307.

Goldberg, et al., "Tissue Ablation with Radiofrequency: Effective Probe Size, Gauge, Duration and Temperature and Lesion Volume", Acad Radio, 1995, vol. 2, No. 5, pp. 399-404.

Melvin A. Astrahan, "A Localized Current Field Hyperthermia System for Use with 192-Iridium Interstitial Implants", Medical Physics, 9(3), May/Jun. 1982.

European Search Report from Application EP 05021939.

International Search Report from EP 05021025.1 dated Mar. 13, 2006.

European Search Report from Application EP 05021935.

Cosman et al. "Theoretical Aspects of Radiofrequency Lesions in the Dorsal Root Entry Zone". Neurosurgery 15:945-950, 1984.

Stuart W. Young, Nuclear Magnetic Resonance Imaging—Basic Principles, Raven Press, New York, 1984.

E.R. Cosman, et al., "Radiofrequency Lesion Generation and its Effect on Tissue Impedance", Applied Neurophysiology, 51:230-242, 1988.

K. Ogata, Modern Control Engineering, Prentice-Hall, Englewood Cliffs, N.J., 1970.

E. Alexander et al., "Magnetic resonance image-directed stereotactic neurosurgery: use of image fusion with computerized tomography to enhance spatial accuracy", J. Neurosurg., 83:271, 276, 1995.

Reidenbach (1995) "First Experimental Results with Special Applicators for High-Frequency Interstitial Thermotherapy", Society Minimally Ivasive Therapy, 4(Suppl 1) :40 (Abstr).

Organ LW. (1976) "Electrophysiologic Principles of Radiofrequency Lesion Making" Appl. Neurophysiol, vol. 39: pp. 69-76.

Livraghi et al. (1995) "Saline-enhanced RF Tissue Ablation in the Treatment of Liver Metastases", Radiology, 205-210.

Solbiati et al. (1995) "Percutaneous US-guided RF Tissue Ablation of Liver Metastases: Long-term Follow-up", Radiology, 197(P): 199.

Solbiati, et al. (2001) "Percutaneous Radio-frequency Ablation of Hepatic Metastases from Colorectal Cancer: Long-term Results in 117 Patients", *Radiology*, vol. 221, pp. 159-166.

Goldberg, et al., "Image-guided Radiofrequency Tumor Ablation: Challenges and Opportunities—Part I", (2001) *J Vasc. Interv. Radiol*, vol. 12, pp. 1021-1032.

McGahan et al. (1995) "Percutaneous Ultrasound-guided Radiofrequency Electrocautery Ablationof Prostate Tissue in Dogs", Acad Radiol, vol. 2, No. 1:pp. 61-65.

Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

European Search Report from Application EP 05021936.9 dated Feb. 6, 2006.

European Search Report from Application EP 05025423.4 dated Jan. 12, 2007.

Bulletin of the American Physical Society, vol. 47, No. 5, Aug. 2002.

European Search Report from Application EP 06019768 dated Jan. 8, 2007.

European Search Report from Application EP 05025424 dated Jan. 23, 2007.

\* cited by examiner

ELECTROSURGICAL SYSTEM EMPLOYING MULTIPLE ELECTRODES AND METHOD THEREOF

CROSS REFERENCE TO RELATED APPLICATION

The present application claims the benefit of priority to U.S. Provisional Application Ser. No. 60/616,967 filed on Oct. 8, 2004 by Orszulak et al., the entire contents of which being incorporated by reference herein.

BACKGROUND

1. Technical Field

The present disclosure is directed to electrosurgical systems, and, in particular, to a radiofrequency electrosurgical system employing multiple electrodes for producing large ablation volumes in tissue or producing multiple ablation volumes in tissue during a single procedure.

2. Description of the Related Art

The use of radiofrequency electrodes for ablation of tissue in a patient's body is known. In a typical situation, a radiofrequency electrode comprising an elongated, cylindrical shaft with a portion of its external surface insulated is inserted into the patient's body. The electrode typically has an exposed conductive tip, which is used to contact body tissue in the region where the heat lesion or ablation is desired. The electrode is connected to a radiofrequency power source, which provides radiofrequency voltage to the electrode, which transmits the radiofrequency current into the tissue near its exposed conductive tip. This current usually returns to the power source through a reference electrode, e.g., a return electrode, which may comprise a large area conductive contact connected to an external portion of the patient's body. This configuration has been described in articles, as for example, a research paper by Cosman, et al., entitled "Theoretical Aspects of Radiofrequency Lesions in the Dorsal Root Entry Zone," Neurosurgery, December 1984, Vol. 15, No. 6, pp 945-950, and a research paper by Goldberg, et al. entitled "Tissue Ablation with Radiofrequency: Effective Probe Size, Gauge, Duration, and Temperature and Lesion Volume" Acad Radio., 1995, Vol. 2, No. 5, pp 399-404. Radiofrequency lesion generators and electrode systems such as those described above are commercially available from Valleylab, located in Boulder, Colo.

To enlarge ablation volumes, electrodes with curved conductive tips have been proposed. Such tips are injected from a cylindrical electrode placed near the targeted or desired tissue volume to produce an off-axis, curved arc within the targeted or desired tissue. In this way, off-axis ablation volumes may be produced away from the central axis of the inserted cannula. The off-axis lesions produced by these off-axis radiofrequency electrodes enlarge the lesion volume away from an axially symmetric, exposed electrode tip. One example of this type of an off-axis electrode is the Zervas Hypophysectomy Electrode available from the company Radionics, Inc., located in Burlington, Mass. Another example of this type of an off-axis electrode is the multiple side-emitting, off-axis electrode made by Radiotherapeutics, located in Mountainview, Calif. The multiple electrode elements range in curved arcs at various azimuthal angles. By making an umbrella of off-axis tip extensions at various azimuthal angles relative to a central insertion cannula, an enlarged lesion volume can be produced. Disadvantages of irregular heat ablation shapes and large central cannula sizes are discussed below.

Also, pairs of electrodes have been inserted into the body in a bipolar configuration, typically in parallel pairs held close to each other. Examples of such bipolar configurations are available from the company Elekta AB, located in Stockholm, Sweden. In such bipolar configurations, one electrode serves as a source and the other serves as a sink for the radiofrequency current from the RF generator. In other words, one electrode is disposed at the opposite voltage (pole) to the other so that current from the radiofrequency generator is drawn directly from one electrode to the other. The primary purpose of a bipolar electrode arrangement is to insure more localized and smaller heat ablation volumes. With such configurations, the ablation volume is restricted to the region between the bipolar electrodes.

Hyperthermia is a method of heating tissue, which contains a cancerous tumor, to thermally non-lethal levels, typically less than 45 degrees Centigrade combined with irradiation of the tissue with X-rays. Such application of mild non-lethal heating in combination with radiation by X-rays enhances destruction of cancer cells while sparing the normal cells from being killed. For hyperthermia, multiple arrays of high frequency electrodes are implanted in tumors. The electrodes are typically placed in a dispersed fashion throughout the tumor volume to cover the tumor volume with uniform heat, which is below the lethal 45 degree level. The electrodes are sequentially applied with high frequency voltage so that each electrode heats in sequence its neighborhood tissue and then shuts off. Then, the next electrode does the same in a time series. This sequence of cycling the voltage through the electrodes continues at a prescribed frequency and for a time period ranging anywhere from minutes to hours. The primary objective of hyperthermia is not to fully ablate tumors by outright heat destruction of the cancerous tumor. On the contrary, its objective is to avoid temperatures above 45 degrees C. anywhere in the treatment volume. The article by Melvin A. Astrahan entitled "A Localized Current Field Hyperthermia System for Use with 192-Iridium Interstitial Implants," in Medical Physics, 9(3), May/June 1982, describes the technique of radiofrequency hyperthermia.

Electrodes with cooled conductive tips have been proposed by Goldberg, et al., in their article referenced above. With cooling, electrode tips generally produce larger lesion volumes with radiofrequency electrodes, which are not cooled.

The electrode systems discussed above are limited by the practical size of lesion volumes they produce. For example, standard single cylindrical electrodes, with cool tips, as described above, make lesion volumes up to 3 to 4 cm in diameter in living tissue such as the liver using cannulae of 1 to 2 mm in diameter and several centimeters exposed tip length. The umbrella lesions made by multiple side-emerging, exposed tips, also produce lesion sizes of 3 to 4 cm volume diameter. A severe hazard of multiple extrusion of side-outlet electrodes is that it produces hemorrhaging by the multiple passes of the side outlet electrodes near the central cannula. Also, at the periphery of such side-emitting electrode lesions, irregularities and undulations in lesion shape and inhomogeneities in temperature around the side-emitted electrode tips produce hot and cold spots over the lesion volume. These may cause focal boiling and charring of tissue with unpredictable and dangerous consequences. For example, consider a large tumor of about 3 to 4 cm diameter in the liver. In such an example, there is a further risk that such undulations and variations in the shape of the periphery of the heat ablation zone would cause portions of the cancerous tumor to be missed by the heat ablation, which of course, would result in continued tumor growth and progression of cancer. Further, a single central cannula, which has one or many side-emitting radiofrequency electrode tips has a diameter, which increases with the number of radiofrequency tips that emerge from it. When the diameter reaches 3 to 4 mm for such a central cannula, there is the disadvantage of increased risk of hemorrhage and/or great pain or discomfort to the patient during insertion of the large central cannula into the tissue.

Thus, a configuration of radiofrequency electrodes which can accomplish ablation volumes in the range of 4 to 6 cm diameter or greater for the purpose of adequately treating large cancerous tumors in the body is necessary to effectively destroy the tumor and combat cancerous cells from spreading. It is further necessary that such an electrode system involve a simple geometry, reduced numbers of tissue insertions, simple planning of needle placement, and simple planning of heat ablation geometry and distribution. Furthermore, an electrode system is desired which can be easily inserted into an organ or through the skin with minimal risk of hemorrhage and discomfort to the patient. An electrode system and method, which produces minimal lesion inhomogeneities to avoid complications of boiling and charring, and which avoids the inadvertent missing of outlying colonies of cancer cells in an irregular tumor is not only desirable, but necessary.

SUMMARY

A radiofrequency (RF) electrosurgical system employing multiple electrodes for producing large ablation volumes in tissue or producing multiple ablation volumes during a single procedure and a method for using the electrosurgical system is provided. The electrosurgical system includes a RF source such as a generator and a controller to direct RF energy delivery from a single generator output to a plurality of electrodes. By employing a multiple electrode in a single procedure, the electrosurgical system can creating larger lesions of 6+cm in diameter or can ablate 2 or more separate lesions simultaneously. The electrosurgical system of the present disclosure allows for the use of multiple small-diameter electrodes instead of a single large-diameter electrode which will minimize the risk of hemorrhaging. Furthermore, by employing multiple electrode, the electrosurgical system can ablate volumes of various shapes and sizes.

The present invention, is a system for heat ablation of tissue in a patient comprises a plurality of electrodes operatively connected to a source of radiofrequency energy and configured to apply RF energy to tissue at a patient site, a plurality of RF current restricting circuits, each circuit coupled between one of the plurality of electrodes and the source of radiofrequency energy, and configured to restrict RF energy to the electrode when the current restricting circuit is enabled and not restrict RF energy to flow to the electrode when the current restricting circuit is disabled, at least one return electrode adapted to contact the patient and configured to return RF energy to the RF source; and a switching mechanism configured to selectively enable each of the plurality of RF current restricting circuits, in one of a sequential and non sequential fashion, wherein the switching mechanism is isolated from each of the current restricting circuits.

In a further embodiment, the switch mechanism comprises a corresponding plurality of optical switching devices.

In a further embodiment, at least one of the current restricting circuits includes a switch configured to direct the flow of RF energy, a plurality of current restrictive devices arranged to restrict RF energy when the switch is disposed in a first position and not restrict RF energy when the switch is disposed in a second position, wherein the switching mechanism is optically coupled to the switch and the switching mechanism selects between said first position and said second position of the switch.

In yet another embodiment, the diodes are used as current restrictive devices.

In yet another embodiment, the plurality of diodes is arranged in an H-Bridge arrangement including a switch disposed therein wherein RF energy is conducted when the switch is-closed.

In a further embodiment, the switch is a transistor.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the present disclosure will be described herein below with reference to the accompanying drawings. In the following description, well-known functions or constructions are not described in detail to avoid obscuring the disclosure in unnecessary detail.

Figure 1:
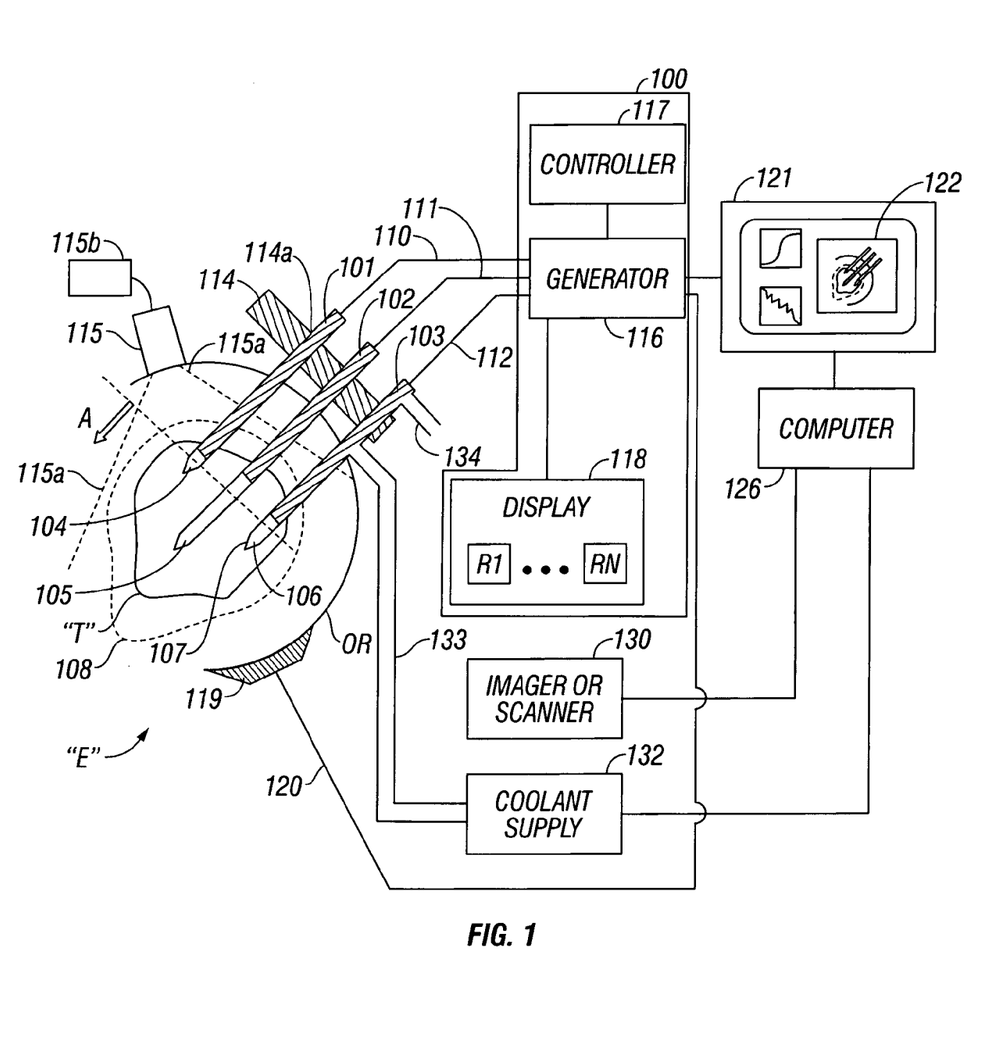
FIG. 1 shows schematically multiple radiofrequency (RF) electrodes positioned in a patient's organ for producing heat ablation of a targeted tissue area in accordance with an electrosurgical system of the present disclosure.

Referring now to FIG. 1, one embodiment of the electrosurgical system using multiple electrodes in accordance with the present disclosure referenced by letter E is generally illustrated. The electrosurgical system E comprises a plurality of electrodes 101, 102, and 103, that are inserted into an organ OR, which may represent any organ in a human body. Their distal tips 104, 105, and 106, respectively, are uninsulated and conductively exposed so that electrical currents induce heating within the tissue or organ OR. A targeted volume of tissue T is shown in sectional view, which may represent, for example, a tumor or other abnormality in a human body.

The electrodes 101, 102, and 103, are individually coupled by wires or cables 110, 111, and 112, as shown, to a generator 100. The generator 100 will include a radiofrequency or high frequency type of generator 116 for generating electrosurgical energy to be applied to the organ. The generator 100 has control elements, e.g., a controller, illustrated generally by block 117, which may, for example, switch radiofrequency power sequentially to each of the electrodes, increase the radiofrequency power output to the electrodes, control temperature when the electrodes or satellite sensors comprise temperature sensors, monitor or control impedance, power, current, voltage, or other output parameters. The generator 100 may include a display provision, illustrated by block 118, within it or as a separate system, for providing a display of heating parameters such as temperature for one or more of the electrodes, impedance, power, current, or voltage of the radiofrequency output. Such individual display readings are illustrated by the reference letters R1, . . . to RN and will generally correspond to the number of electrodes associated with the system.

It is to be appreciated that the energy source 116, the controller 117 and display 118 may be disposed in a single housing or implemented as separate components. For example, in one embodiment, the controller 117 may be a separate component adapted for receiving a single constant voltage from a energy source wherein the controller varies parameters of the energy to obtain a desired output.

A reference electrode 119, e.g., a return electrode, is also shown, which may be placed in contact with the skin of a patient or the external surface of the organ OR with a connection 120 to the generator 100. In one embodiment, this serves as a path for return current from the generator 100 through the electrodes 101, 102 and 103.

The electrodes 101, 102 and 103 in accordance with one exemplary embodiment, comprise rigid shafts, which may be easily urged into the body tissue. They terminate in tissue-penetrating pointed tips 107 on electrode ends 106. They have a portion of their external shaft surface of insulated material indicated by the hatched line areas on electrodes 101, 102 and 103. The distal tip referenced by 104, 105, and 106 for each electrode comprise conductive metal and are connected through the shafts 101, 102 and 103 to the connection cable 110, 111, and 112 respectively, and thereby to the generator output source 100.

According to the present disclosure and illustrated in FIG. 1, the electrodes 101, 102 and 103 may be placed in a single target, e.g., a tumor. The heating effect of the multiple electrodes is similar to that accomplished by one large single electrode. The individual electrodes 101, 102 and 103 cause less trauma and do not induce hemorrhaging when they penetrate the organ OR because of their smaller size. Yet when they are connected to a radiofrequency voltage source, they represent an effectively much larger electrode. In this way, larger heat volumes, and therefore ablation sizes, may be achieved.

As an illustration, in FIG. 1 the targeted volume is represented in sectional view by the line T. Consider that it is desired to ablate the targeted region T by fully engulfing it in a volume of lethal heat elevation. The targeted area T may be, for example, a tumor which has been detected by image scanner 130. CT, MRI, or ultrasonic image scanners may be used, and the image data transferred to computer 126. As an alternate example, an ultrasonic scanner head 115 may be disposed in contact with OR to provide an image illustrated by lines 115A. Data processor 115B may be connected to display devices to visualize the tumor T and/or ablation zone 108 in real time during the ablation procedure. The image representation of the scan may be displayed on display unit 121, which may, for example, be a CRT screen. Slice renderings through the organ OR may be displayed in window 122 to represent the size and position of targeted volume T. Placement of the electrodes 101, 102 and 103 may be predetermined based on such image data as interactively determined by real-time scanning of organ OR. The electrodes may be inserted into the tissue by freehand technique by a guide block with multiple hole templates, or by stereotactic frame or frameless guidance. A stereotactic guide is shown schematically by element 114. Guide holes such as 114A for electrode 101 aim it to the desired targeted position based on image data.

In accordance with the present disclosure, electrodes 101, 102 and 103 are independently activated with radiofrequency energy from generator 100. They thus will act as an effectively larger electrode. Their relative positions and orientations enable different positive shapes and sizes of ablation volumes to be made than could possibly be made from a single larger electrode. For example, in FIG. 1 the dashed line represents the ablation isotherm in a sectional view through organ OR. Such an ablation isotherm may be the surface achieving temperatures of approximately 50 degrees or greater. At that temperature range, sustained for about 30 seconds to several minutes, tissue cells will be killed or ablated, in accordance with the paper of Cosman, et al., referred to above. The shape and size of the ablation volume illustrated by dashed line 108 may accordingly be controlled by the configuration and/or placement of the individual electrodes, the geometry of the exposed tips 104, 105, and 106, the amount of RF power applied, the time duration that the power is applied, cooling of the electrodes, and so on.

In each of the examples, also, the electrodes may be cooled by a coolant, such as chilled circulating saline, within them. A coolant supply 132 will supply coolant to the electrode via connection 133, e.g., tubing. The coolant will circulate among the electrodes and either return to the coolant supply or be discharged via connection 134. Such electrodes are described in U.S. Pat. No. 6,506,189 entitled "COOL-TIP ELECTRODE THERMOSURGERY SYSTEM" issued to Rittman, III et al., on Jan. 14, 2003, the contents of which are herein incorporated by reference. Thereby, the multiple electrodes represent an effectively larger, cooled radiofrequency structure. With adaptations a much larger radiofrequency ablation may be accomplished. Multiplicities of cluster electrodes may also be implemented for other geometric or clinical advantages. Cluster electrodes are described in U.S. Pat. No. 6,530,922 entitled "CLUSTER ABLATION ELECTRODE SYSTEM" issued to Cosman et al., on Mar. 11, 2003, the contents of which are herein incorporated by reference.

The use of a multiplicity of N electrodes increases the overall conductive exposed tip area by which to send RF current for heating into the tissue. This increases the heating power that may be delivered and thus increases the size of the ablation volume possible. Furthermore, the cooling capacity of a multiplicity of N electrodes also increases as the number N increases. Increasing the number of electrodes increases the cooling surface area near the electrodes. Thus, the heat sinking effect from a plurality of electrodes is greater than the heat sinking effect from a single electrode element. This enables the lesion size to be expanded accordingly.

An advantage of a multiplicity of smaller electrodes versus insertion of a single large electrode is that the smaller electrodes will produce less chance of hemorrhage. The arrangement of their geometry may also be tailored to the clinical application. Insertion of several small gauge electrodes is less painful, uncomfortable, and risk-inducing than insertion of one large, equivalent radiofrequency electrode. For example, insertion of a cluster of several 18 gauge or 1.25 mm diameter pointed radiofrequency electrodes into the liver produces very low risk of hemorrhage and low discomfort. Insertion of an equivalent, but much larger single electrode, which may have a diameter of, for example, 0.25" or 6.4 mm, would have a higher risk of hemorrhage and would be very uncomfortable for the patient if the electrode were inserted percutaneously.

Figure 2:
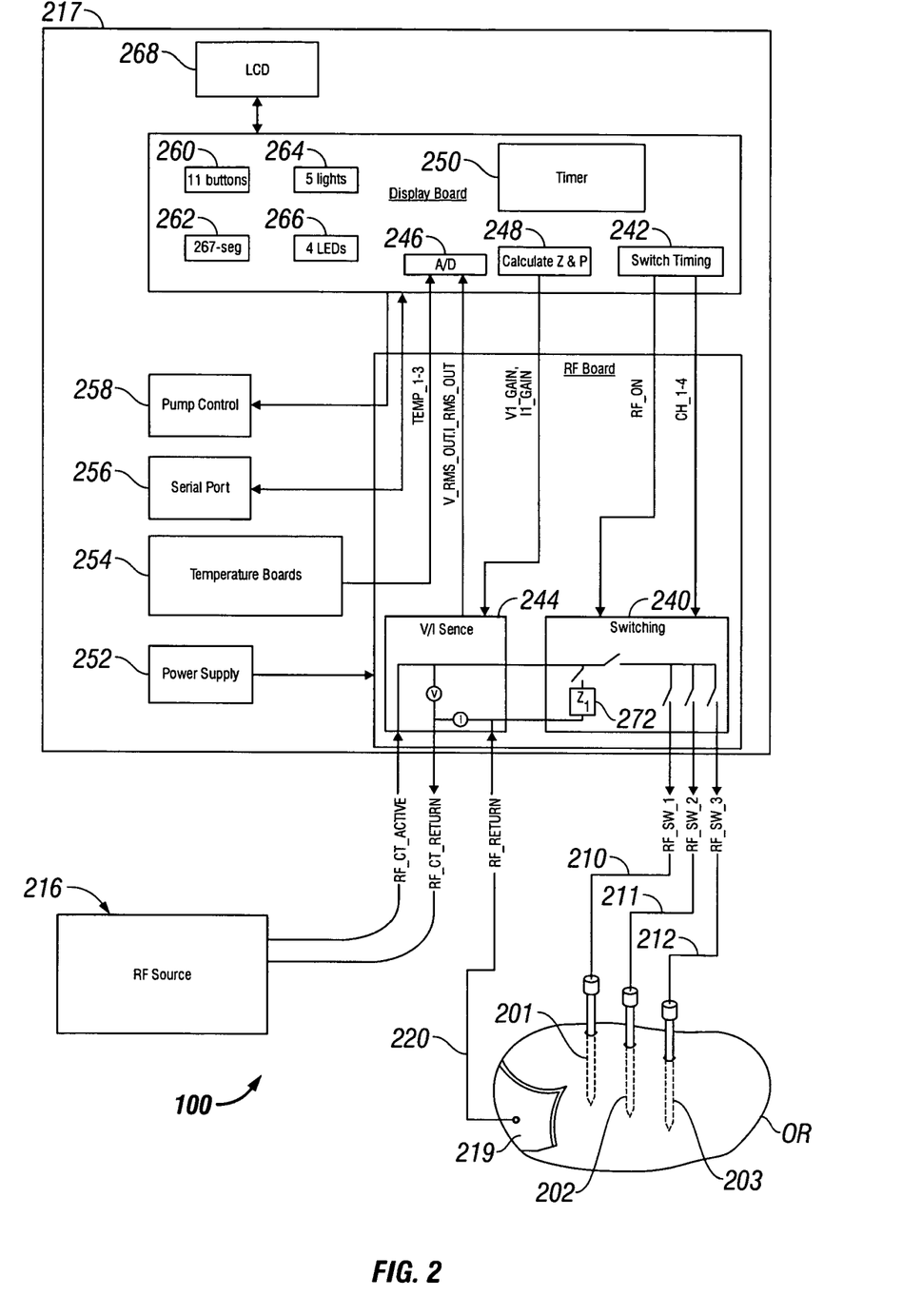
FIG. 2 is a schematic diagram of a electrosurgical generator in accordance with the present disclosure.

Referring to FIG. 2, a schematic diagram of generator 100 of the present disclosure is shown. The generator 100 includes a radiofrequency source 216 for supplying RF energy and a controller 217 for controlling the supply of RF energy to the multiple electrodes, the operation of the coolant supply and for the display and entry of control parameters. By way of one example, the RF source 216 may be a radiofrequency generator with frequency between about 100 kilo Hertz to several hundred mega Hertz. An example of such a generator is the lesion generator available from Valleylab of Boulder, Colo. It may have power output ranging from several watts to several hundred watts, depending on the clinical application.

The controller 217 includes a switching mechanism 240 including a plurality of output channels RF_SW_1, RF_SW_2, RF_SW_3 for individually supplying RF energy to the multiple electrodes 201, 202, 203. The switching mechanism 240 further includes an internal load 272 for dissipating RF energy in certain situations when any of the plurality of electrodes can not be activated. Control of the switching mechanism is provided by switch timing circuit 242 which is programmed with executable instructions for switching the RF energy output among the plurality of channels or the internal load, the sequence of which will be described in detail below in relation to FIGS. 4 and 4A. The controller 217 further includes V/I sense circuitry 244 for providing the RF energy from the RF source 216 to the switching mechanism 240 and for measuring the current and voltage supplied to an active electrode of the multiple electrodes. The V/I sense circuitry 244 will send the measured values of current and voltage, e.g., I_RMS_OUT, V_RMS_OUT, to module 246 which may be a analog-to-digital converter. The digital values of the current and voltage will then be sent to module 248 to calculate impedance and power at the active electrode, which will further be used for controlling the RF energy output as will be described below.

Figure 2A:
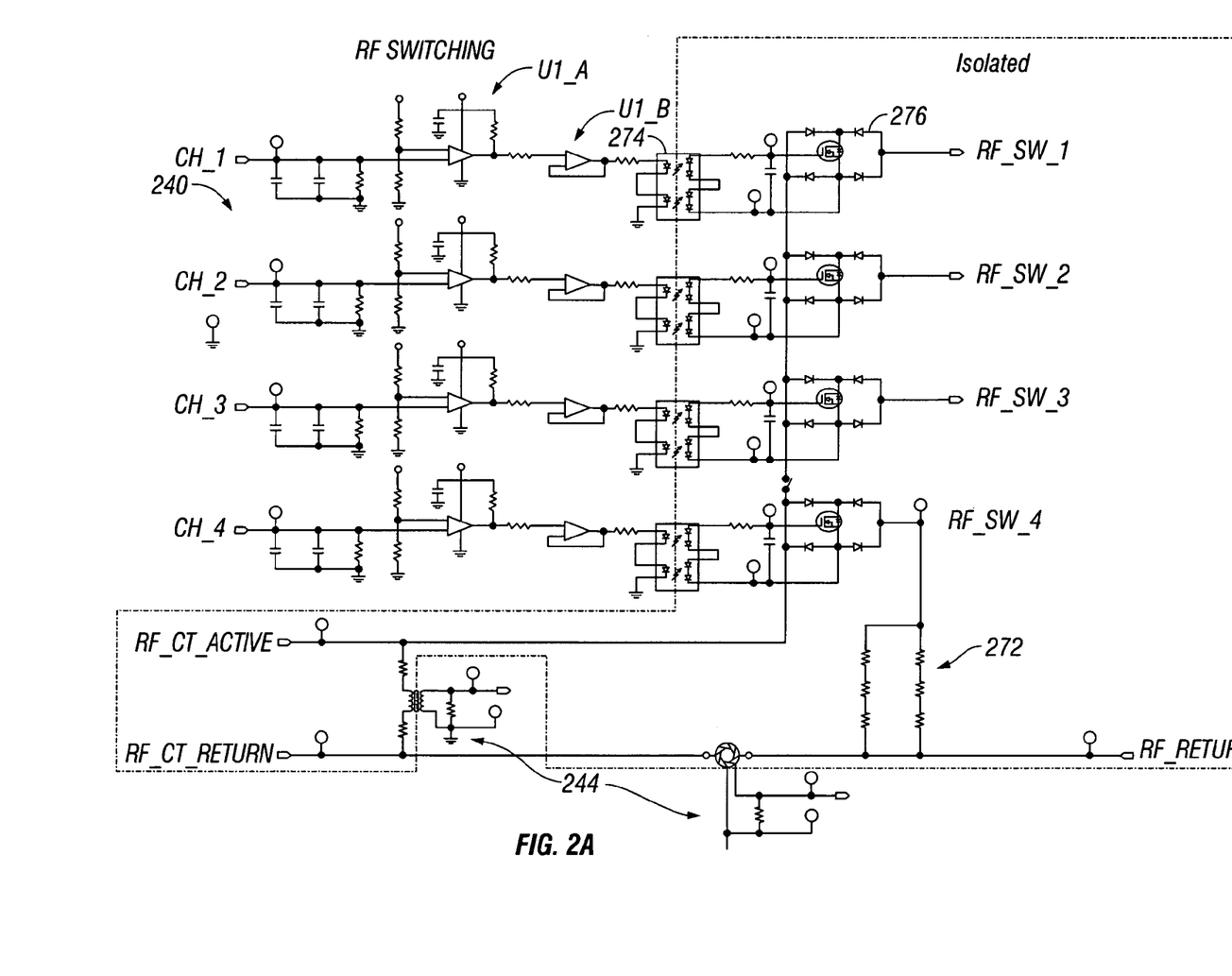
FIG. 2A is a schematic diagram of the switching mechanism shown in the electrosurgical generator of FIG. 1.

Referring to FIG. 2A, a detailed schematic diagram of the switching mechanism 240 and V/I sense circuitry 244 is illustrated. The switching mechanism 240 includes a plurality of output channels for supplying RF energy to an electrode coupled to the channel. The circuitry CH_1, CH_2, CH_3 and CH_4 for each channel is substantial identical, and therefore, only one channel CH_1 will be described in detail. When the controller determines that channel 1 is to be activated, a digital high signal will be sent to terminal CH_1. Comparator U1-A will then send a digital high signal to buffer U1-B which will activate electro-optical device 274. An example of such an electro-optical device is represented by photo-voltaic isolator, part PVI5033R commercially available from International Rectifier of El Segundo, Calif. The electro-optical device 274 will in turn activate coupling circuitry 276 for coupling the RF energy, supplied via connection point RF_CT_ACTIVE, to an attached electrode via channel output R_SW_1. In contrast to the conventional electromechanical switching means, e.g., a relay, the electro-optical switching means 274 requires less volume to implement, rendering a size advantage by reducing space requirements, provides for a faster means for switching RF energy and increases reliability by eliminating the cold switch method required by the electromechanical means.

Channels 1, 2 and 3 supply RF energy to the active electrode while channel 4 drives an internal load 272 which dissipates RF energy in certain situations when an active electrode cannot be activated.

Figure 2B:
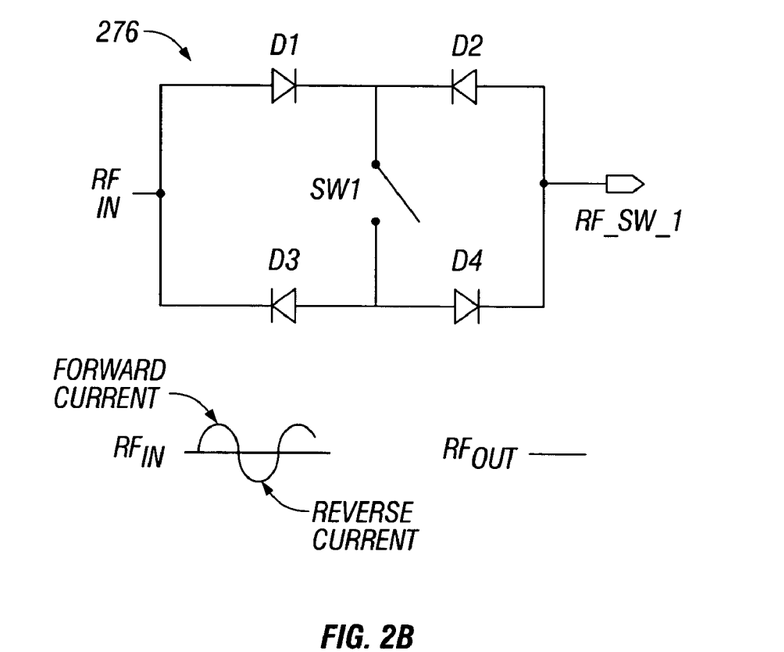
FIG. 2B is a schematic diagram of a coupling mechanism for coupling the switching mechanism of FIG. 2A to an electrode with no RF energy conducted to the tissue site.
Figure 2C:
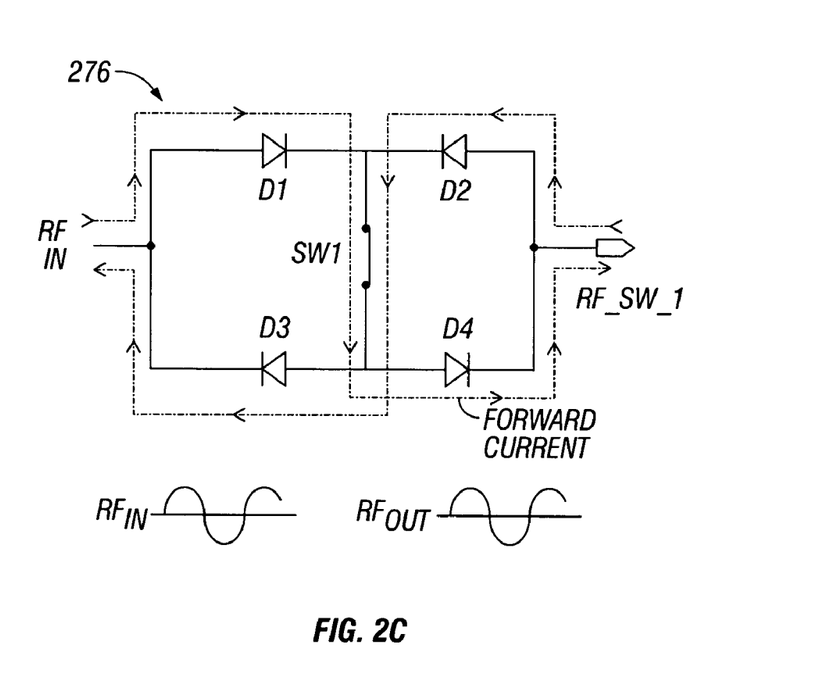
FIG. 2C is a schematic diagram of a coupling mechanism for coupling the switching mechanism of FIG. 2A to an electrode with RF energy conducted to the tissue site.

The coupling circuitry 276 is shown in more simplified form in FIGS. 2B and 2C for facilitating discussion of the principles of the disclosure. The coupling circuitry 276 includes a plurality of diodes D1, D2, D3, D4 arranged in an H bridge arrangement with a switch SW1 disposed across the bridge. Preferably, the switch SW1 is a transistor as shown in FIG. 2A, configured using a power MOSFET technology part, exemplary part IRFBA22N50A, commercially available from International Rectifier of El Segundo, Calif. As will be described, when the switch SW1 is open, the diodes will block the flow of current to the attached electrode and, when the switch SW1 is closed, the current will flow to the attached electrode. RF current, e.g., RFIN, consists of electrical energy flowing first in one direction, and then another, designated as forward and reverse for this discussion. As illustrated in FIG. 2B, the RF energy supplied is essentially a sinusoidal waveform, where when the wave is in the positive region, current flow is blocked in a forward direction, and when the wave is in the negative region, current flow is blocked in the reverse direction. Therefore, as shown in FIG. 2B, when switch SW1 is open, current flow is blocked in both the forward and reverse directions. Current will not flow through diode D1 with a positive wave of the sinusoidal waveform, due to the reverse bias blocking action of diode D2. Similarly, current will not flow through diode D3 with a negative wave of the sinusoidal waveform, due to the reverse bias blocking action of diode D4. As a result of switch SW1 being open, RF energy is subsequently blocked and will not reach the attached electrode. Therefore, the H bridge arrangement of diodes will block current flow in both directions when switch SW1 is open.

When energy is to be applied to the attached electrode, electro-optical device 274 will be activated which will bias switch SW1 to close, as illustrated in FIG. 2C. For forward current flow, diode D1 is forward biased, i.e., ON, and current flows through switch SW1 and through diode D4 which is also ON. When the current reverses direction, diodes D1 and D4 are biased OFF and diodes D2 and D3 are biased ON allowing current to flow. Therefore, as a result of switch SW1 being closed, RF energy and current will flow to the attached electrode regardless of the direction of current.

The switching mechanism 240 provides a more efficient means of delivering RF energy to clinical sites for real time RF switched delivery applications. Less power loss is consumed by the switching mechanism 240 due to the use of passive components, e.g., diodes D1-D4, to route the flow of RF energy and one actively switched device to turn the RF energy ON or OFF in the coupling circuitry 276. Conventional real time techniques to switch RF energy use a plurality of power devices, e.g., power FETs, for actively switching the fundamental RF frequency. As a result, the conventional switching technique dissipates more power due to increased switching losses and delivers less power to the tissue.

The electro-optical switching technique of the present disclosure, in real time switched applications, provides a higher means of isolation, e.g., lower leakage, between the RF source and the patient connection at the tissue site. By providing an electro-optical device, a low fixed capacitance and high dielectric insulation is established intrinsic to the electro-optical device, due to the substrate rating of the electro-optical device. This avoids an increased leakage path, which is RF frequency dependent to protective earth. Conventionally, the increased leakage is due to the magnetically coupled power FET drive and the associated power FET device miller capacitance, which presents RF leakage coupling with the driven FETs. Furthermore, the electro-optical switching results in less leakage than would normally occur through a relay.

The electro-optical device 274, along with the V/I sense circuitry 244, provides a patient connective isolation barrier from the RF source protective earth return to avoid a potential patient hazard to alternate site burns due to RF leakage.

Referring back to FIG. 2, timer 250 will be employed to measure the duration of RF output activation for each channel and to measure a total procedure time.

The controller 217 will further include power supply 252 for supplying power to the various components of the controller 217; at least one temperature board 254 for determining a temperature at a tip of an electrode when the electrode includes a temperature sensor such as a thermocouple; a serial port 256 for coupling the controller 217 to a computer for downloading values from the controller 217 or for reprogramming the controller 217; and a pump control mechanism 258, e.g., a relay, for controlling flow from a coolant supply when a cool-tip electrode is employed. Furthermore, the controller 217 includes a plurality of input and output devices 260, 262, 264, 266, 268 for entering parameters relating to a predetermined procedure and for displaying values measured during the procedure, for example, temperature, current, voltage, procedure time, etc.

A series E(N) of N electrodes 201, 202, 203 is shown inserted into organ or bodily element OR and coupled to the switching mechanism 240. These electrodes may be, for example, metal shafts with an insulated portion, except for an exposed distal tip, as described above. They may have self-penetrating or tissue-piercing, pointed tips. The individual electrodes may or may not have pointed tissue-piercing tips, as the clinical need and technique requires. For example, in the brain, a rounded, smooth-tipped electrode will penetrate brain tissue and could provide less risk of hemorrhage from penetrating blood vessels. For percutaneous insertion, pointed electrodes or pointed guide cannulae followed by round-tipped electrodes may suit the clinical technique.

Each electrode 201, 202, 203 is individually coupled, via cables 210, 211, 212 respectively, to an output channel of switching mechanism 240. A reference area electrode 219 is shown contacting a surface of the organ OR. It is connected by element 220 to the controller 217 which may act to return radiofrequency current to the power generator 216 or cooling fluid if area electrode 219 is also a cooled type.

Such a configuration may be clinically useful if a large volume or block of tissue is to be ablated. For example, if the electrodes 201, 202, 203 are inserted in a nearly parallel array in an organ such as the liver, and a reference electrode such as 219 is a plate electrode placed on the surface of the liver roughly parallel to the electrode array E(N), then an effectively "parallel plate" electrode configuration is achieved. In that case, a relatively uniform and large block of ablative heating volume may be induced between the electrode array E(N) and the plate electrode 219. Within that volume, a cancerous tumor or other tissue abnormality, which is desired to be ablated, would be completely destroyed. Variations in electrode placement and geometry, such as parallel or non-parallel, may be used to create changes in shape of the ablation volume as clinical needs require. Electrode insertion from varied directions may help in avoiding critical anatomical structures or obstructions while still increasing the number of electrode elements to achieve the desired lesion size. Variations in the degree of exposed conductive tip for electrode elements may vary according to a clinical targeted site.

Figure 3:
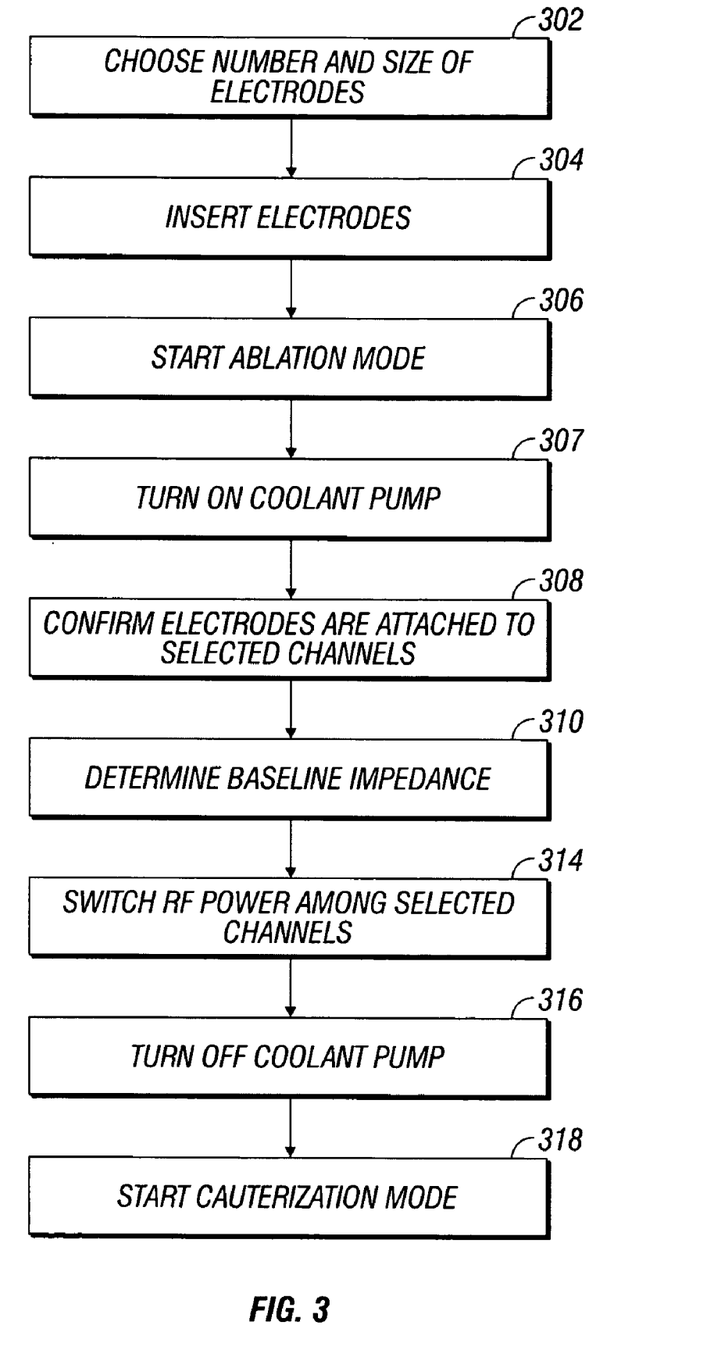
FIG. 3 is a flowchart illustrating an operation of the electrosurgical system.

FIG. 3 illustrates an operation of the electrosurgical system using multiple electrodes, as shown in FIG. 2, in accordance with one embodiment of the present disclosure. At the outset, depending on the clinical conditions or requirements, an appropriate or desired configuration of the multiple electrodes is selected by the clinician (step 302). At this stage, determinations as to the following factors are considered by the clinician, which are provided by way of example: (a) the number of electrodes; (b) their relative geometry, individual electrode sizes and tip exposures; (c) whether the electrodes are desired in one predetermined cluster or individual sizes and configurations for individual placement within the organ; (d) the determination whether cooled or non-cooled electrodes are desired. Step 302 may also represent the steps of processing image scan data from a CT, MR, ultrasound, or other type of scanner to determine the position of a targeted volume such as a tumor within the patient's body and the desired approach, placement, size, and number of electrodes. This may be done on a computer graphic workstation using 3D graphics and stereotactic orientation and methods, as illustrated by the XKnife, StereoPlan, or XSeed treatment planning systems of Radionics, Inc., of Burlington, Mass.

The stereotactic positioning of the multiple electrodes may be preplanned on the workstation. The heat isotherms and ablation volume and time-course of the ablation may be calculated and displayed on the workstation as part of the preplan. Based on historical or empirical information, the clinician may in step 302 determine the desired power to be delivered to the tissue, the temperature as measured by the electrode or measured elsewhere in the tissue by satellite temperature-sensing electrodes, the desired time duration of radiofrequency heating, and the characteristics of impedance, to determine cut-offs and control against boiling, charring, and other untoward effects. This may be done as a preplan using 3D computer graphics of the entire heating process.

The step of inserting the multiple electrodes is represented by step 304 in FIG. 3. The electrodes may be placed individually or in unison within the body tissue, as described above. Real-time imaging may be utilized, such as ultrasound, MRI, or CT, during placement of the electrodes to determine their proper position within a targeted volume of tissue. The electrodes are inserted to a desired depth during this step.

In step 306, the clinician will select the ablation mode and the procedure timer will be set to zero. In step 307, the controller 217 will activate pump control 258 to provide cooling to the electrodes. Preferably, the electrodes are "piped" in series in that coolant flows from the coolant supply through the first electrode to the second electrode and to the third electrode; then is either discharged or flows back to the supply. The ablation process will not begin until all selected electrodes are below a predetermined limit, e.g., 20° C. This predetermined temperature limit may be user selectable or selected by the controller based on tissue type, procedure selected, etc.

The controller 217 will sequence power through each selected channel of the switching mechanism 240 to determine if an electrode is attached to the channel (step 308). Here, the controller 217 will apply a pulse of RF power approximately for about 600 ms to the first selected channel. If the measured impedance is below a predetermined limit, the control mechanism will confirm an electrode is attached and repeat the process for each selected channel.

Next, the controller 217 will determine a baseline impedance for each electrode attached (step 310). The controller 217 will apply power to the first selected channel for approximately 30 seconds and record the lowest impedance value measured in the first 10 seconds as the baseline impedance for that channel. Preferably, the controller 217 will average every 10 impedance data points during the 10 second period and save the lowest average as the baseline impedance. After 30 seconds, the controller 217 will move to the next selected channel and repeat the process to determine the baseline impedance. The controller 217 will move through all selected channels until a baseline impedance is determined for all the channels.

Figure 4:
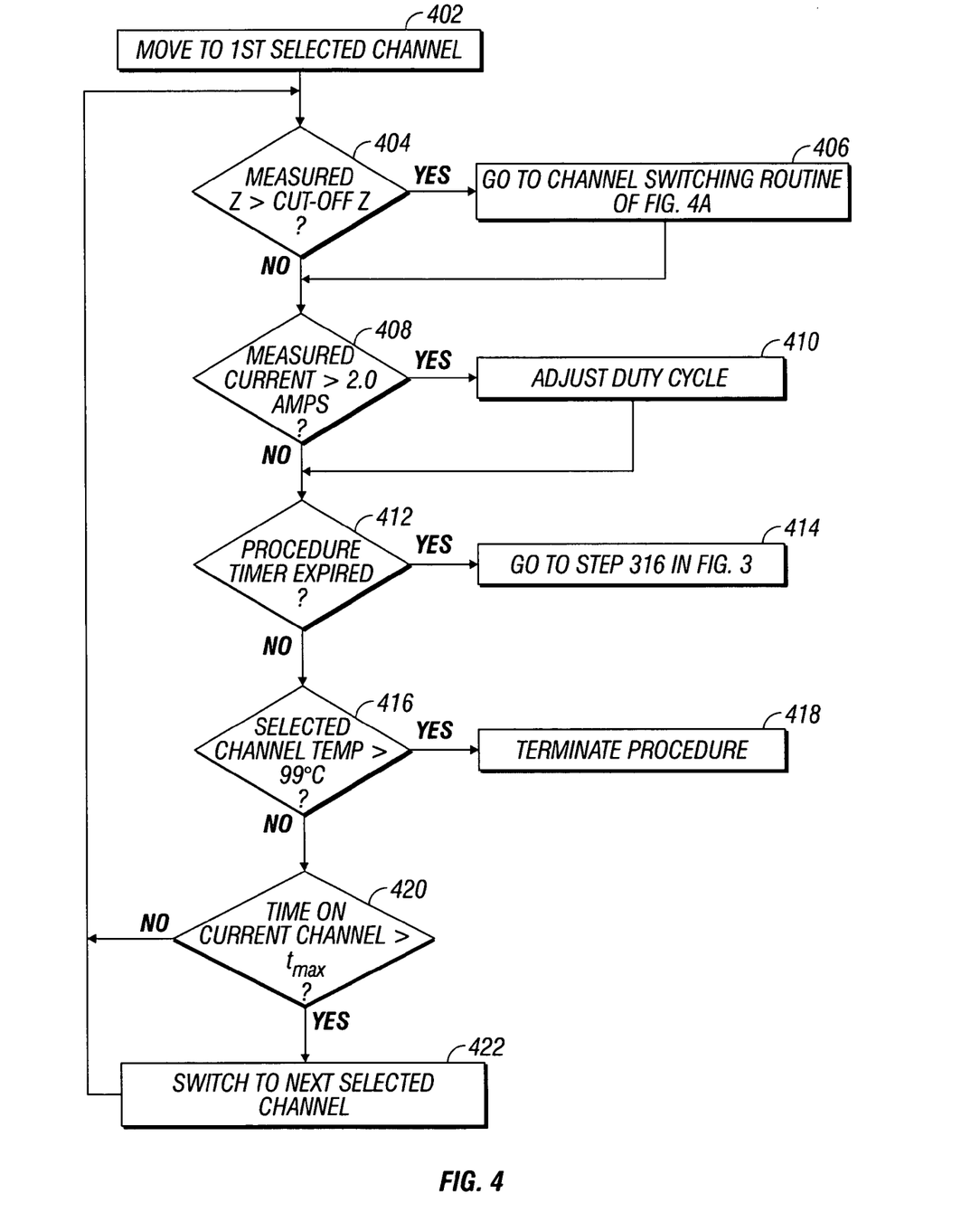
FIG. 4 is a flowchart illustrating an ablation procedure in accordance with the present disclosure.

Once all the selected electrodes are below the predetermined temperature limit, the ablation process will begin and the controller 217 will switch RF power among the selected channels according to the algorithms illustrated in FIGS. 4 and 4A (step 314). Referring to FIG. 4, the controller 217 will apply power to the first selected channel, e.g., RF_SW_1, to active the first electrode 201 (step 402). Module 248 will determine the impedance at electrode 244 and controller 217 will compare the measured impedance to an impedance cut-off for the selected channel (step 404). The impedance cut-off will be based on the baseline impedance measured for the selected channel. If the baseline impedance is less than 100 ohms, the impedance cut-off will be set at the baseline impedance plus an impedance differential, e.g., 30 ohms. If the baseline impedance is greater than 100 ohms, the impedance cut-off will be set at the baseline impedance plus 30 percent of the measured baseline impedance. If the instantaneous measured impedance at the selected electrode is greater than the cut-off impedance, e.g., an over-impedance condition, the controller 217 will load the channel switching routine to determine if power should be applied to the next channel or to the internal load 272 (step 406).

Figure 4A:
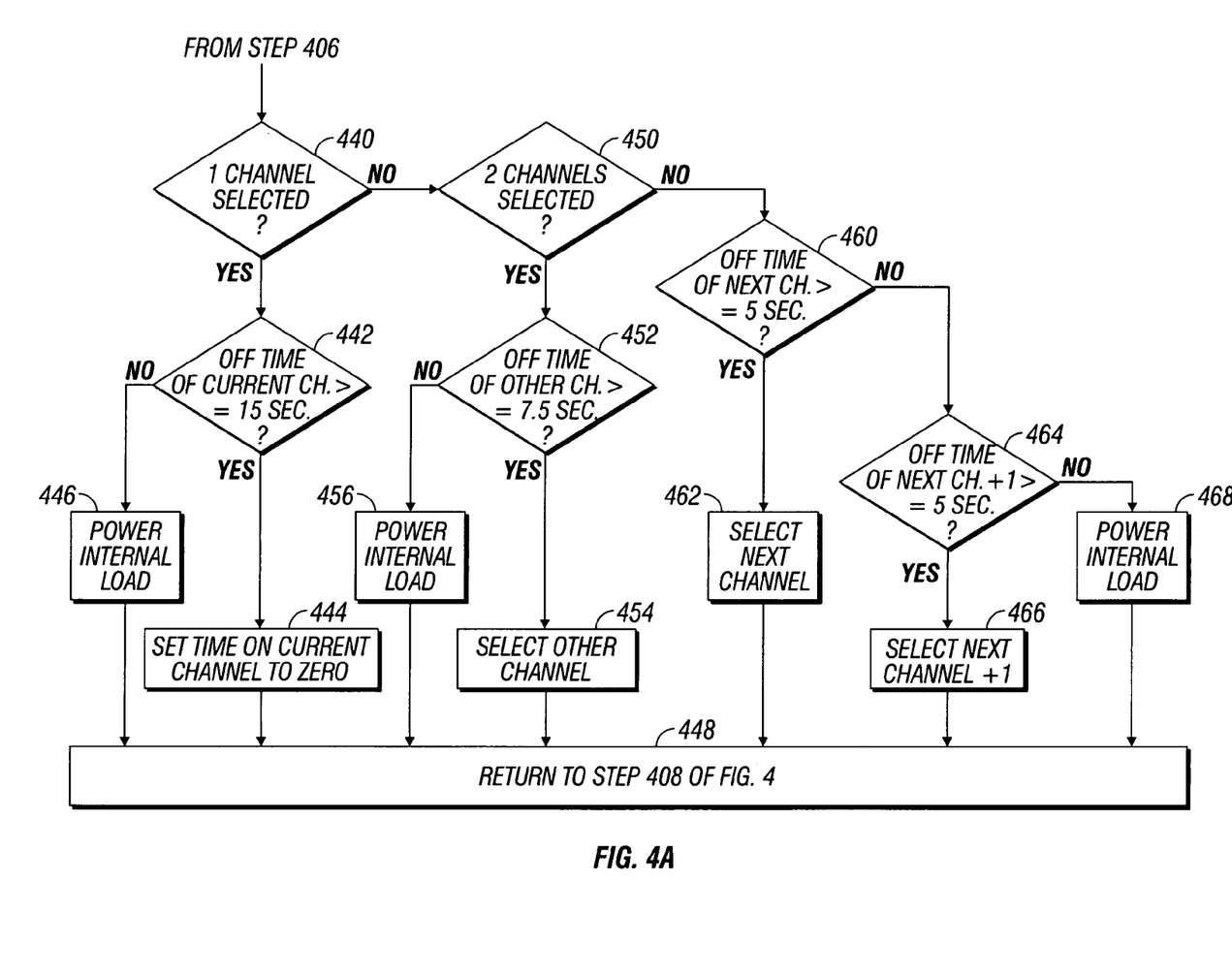
FIG. 4A is a flowchart illustrating a channel switching routine in accordance with the present disclosure.

Referring to FIG. 4A, the switching among electrodes will depend on how many electrodes are selected for the procedure. Each electrode employed in the procedure will have a minimum off time following a period of activation. The minimum off time for each electrode will equal a predetermined period of time, e.g., 15 seconds, divided by the number of selected electrodes. Therefore, in step 440, if one channel is selected for the procedure, the controller 217 will determine if the off time for the current channel is greater than or equal to 15 seconds. If the off time for the current channel is greater than or equal to 15 seconds (step 442), energy will be applied to the current channel selected and the time on for the current channel will be set to zero (step 444) and the process will return to step 408 of FIG. 4. If the off time for current channel is less than 15 seconds, the controller 217 will power the internal load (step 446) and the process will return to step 408 of FIG. 4. If two channels are selected (step 450), the controller 217 will determine if the off time for the other channel is greater than or equal to 7.5 seconds. If the off time for the other channel is greater than or equal to 7.5 seconds (step 452), energy will be applied to the other channel selected (step 454) and the process will return to step 408 of FIG. 4. If the off time for current channel is less than 7.5 seconds, the controller 217 will power the internal load (step 456) and the process will return to step 408 of FIG. 4.

If three channels are selected for the ablation procedure, the controller 217 will determine whether the off time of the next channel in sequence is greater than or equal to 5 seconds (step 460). If the off time for the next channel in sequence is greater than 5 seconds, the controller 217 will select and apply energy to the next channel (step 462) and the process will return to step 408 of FIG. 4. If the off time for the next channel is less than 5 seconds, the controller 217 will determine the off time for the next channel plus one in the sequence of selected channels (step 464). If the off time for the next channel plus one is greater than or equal to 5 seconds (step 464), energy will be applied to the next channel plus one (step 466) and the process will return to step 408 of FIG. 4. If the off time for next channel plus one is less than 5 seconds, the controller 217 will power the internal load (step 468) and the process will return to step 408 of FIG. 4.

In an alternative embodiment, instead of powering the internal load if no channel is available, the generator may stop supplying RF energy for a predetermined period of time or simply the generator may shut down.

Referring back to step 404, if the measured impedance at the selected electrode is less than the cut-off impedance, power will continue to be applied. Next, the controller 217 will determine if the current being applied to the selected channel is above a predetermined current limit (step 408). If the current applied to the selected electrode is above the predetermined current limit, e.g., 2 amps, the controller 217 will duty cycle with the internal load to create a 2 amp average (step 410); otherwise, the process will go to step 412. In step 412, the controller 217 will determine if the total procedure time has expired. If the procedure time has expired, the process will return to step 316 of FIG. 3 and the ablation process will be complete. If the process time has not expired, the controller 217 will determine if the selected channel temperature has gone above a predetermined temperature limit, e.g., 99° C. If the selected channel's temperature has gone above the predetermined temperature limit, the selected channel will be turned off and the ablation procedure will be terminated (Step 418). If the temperature of the selected channel is satisfied, the controller 217 will determine if the selected channel has been activated longer than the maximum time allowable for the channel $t_{max}$ (step 420). If the on time exceeds the maximum allowable time, e.g., 30 seconds, the controller 217 will switch to the next selected channel (step 420); otherwise, the process will return to step 404 and process the selected channel again.

Once the procedure time has expired, the ablation of the target volume or volumes should be complete and the process will return to step 316 of FIG. 3. Once the ablation mode is completed, the controller 217 will deactivate pump control 258 and the pump will stop, ceasing the flow of coolant. The clinician will then enter the cauterization mode to remove the electrodes (step 318).

Conventionally, two people are required to cauterized the channel created in the tissue or organ by the insertion of an electrode. One person is required to remove the electrode from the surgical site and a second person is required to control power at the generator to attempt to maintain a predetermined temperature at the tip of the electrode as the electrode is being withdrawn. A method of the present disclosure overcomes the requirement for two people by automatically controlling the temperature of the selected electrode as it is being withdrawn.

Figure 5:
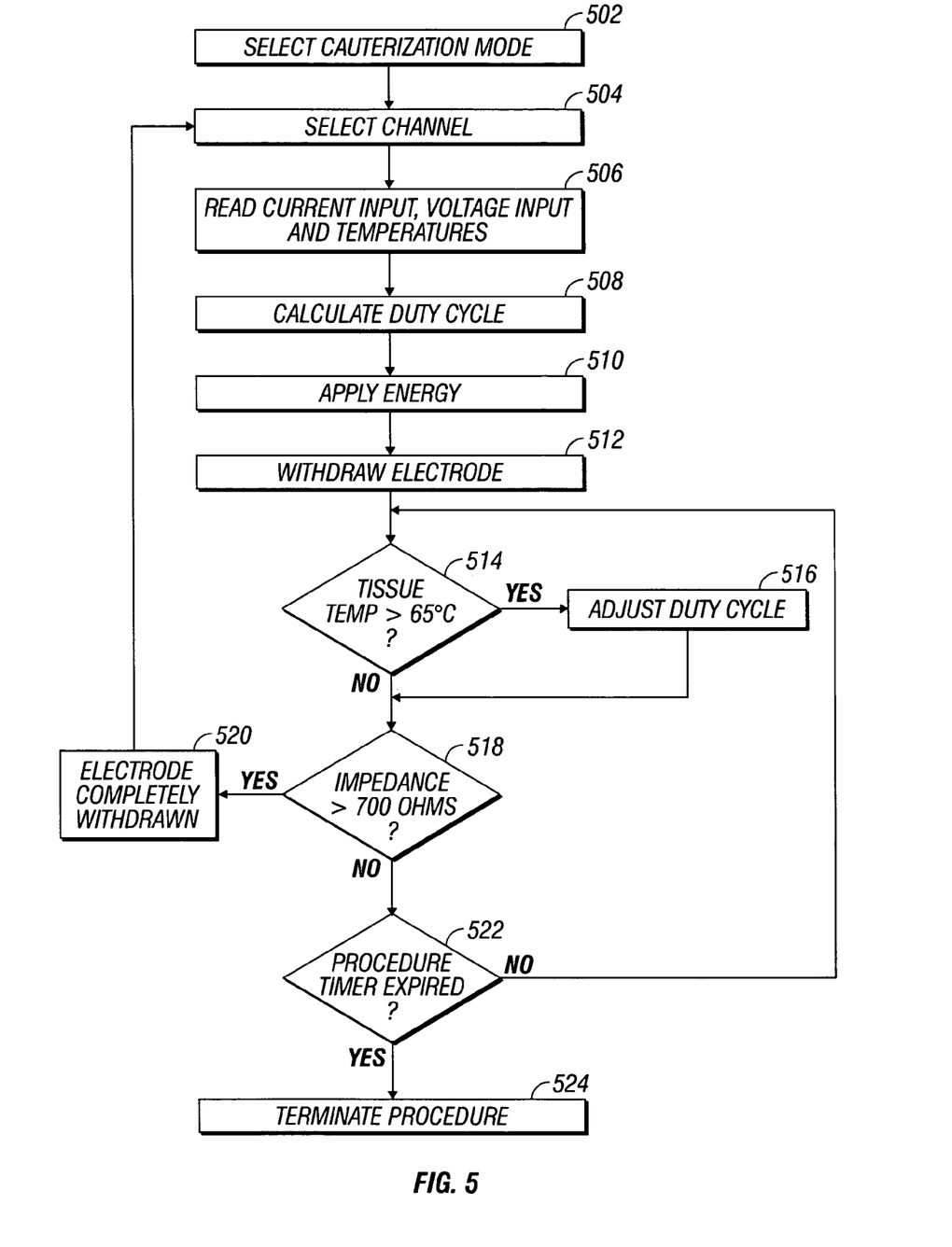
FIG. 5 is a flowchart illustrating a cauterization procedure in accordance with the present disclosure.
Figure 6:
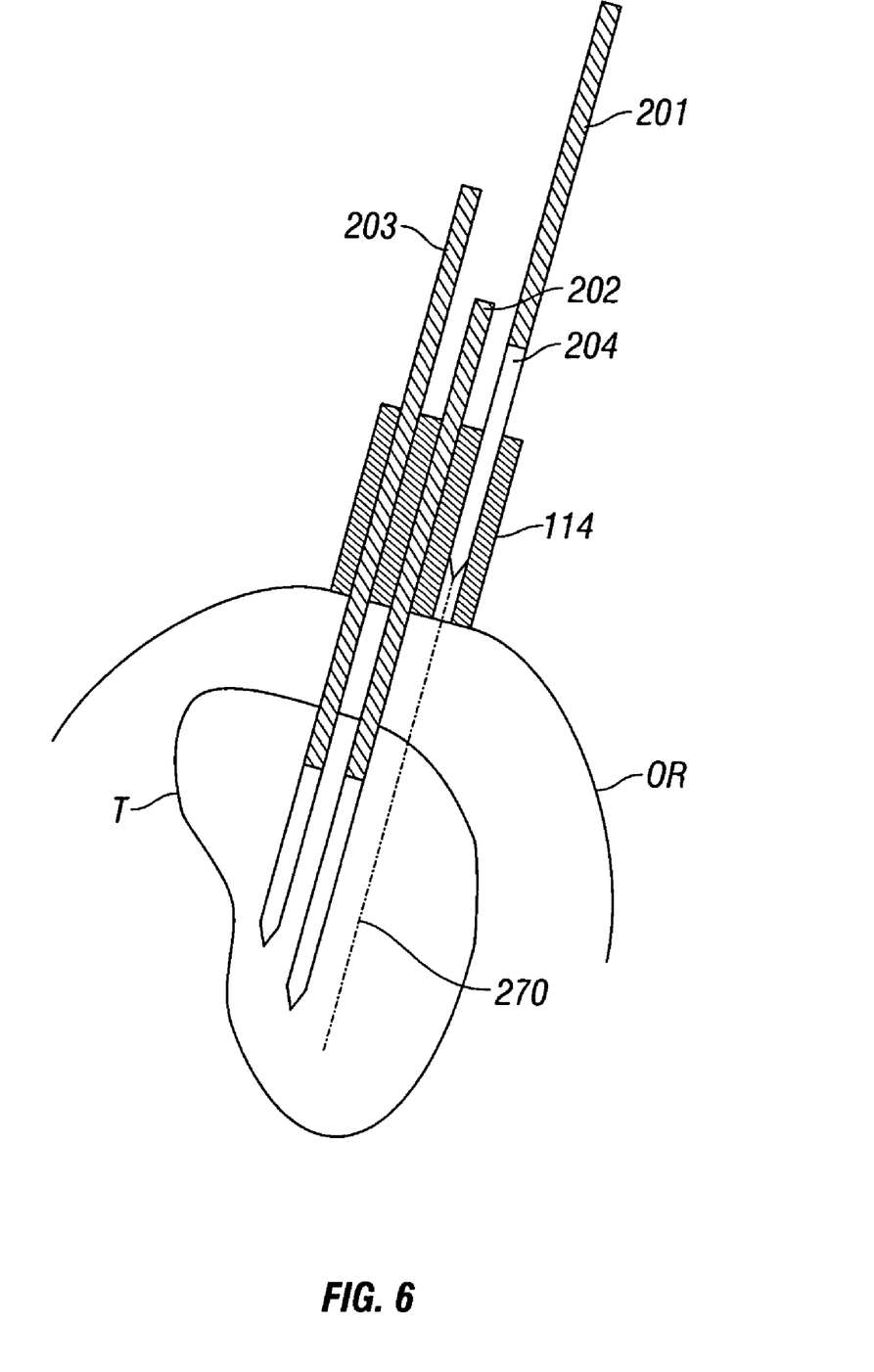
FIG. 6 illustrates a partial sectional view illustrating withdrawal of a single electrode during a cauterization procedure in accordance with the present disclosure.

Referring to FIG. 5, the clinician will enter the cauterization mode (step 502) and select the channel of the electrode to be withdrawn (step 504). In step 506, the controller 217 will read the current, voltage and temperature at the selected electrode. The controller 217 will then calculate the duty cycle of the power to be applied to maintain a desired temperature of the exposed portion 204 of the selected electrode 201 as illustrated in FIG. 6. In step 510, power is then applied to the electrode 201 and the clinician will begin to withdraw the electrode (step 512). As the electrode 201 is being withdrawn, power is being applied to cauterize the channel 270 created by the insertion of the electrode 201. During the withdrawal process, the controller 217 will continuously monitor the temperature at the electrode tip 204 to ensure the temperature does not go below a predetermined limit, e.g., 65° C. (step 514). If the temperature at the tip 204 goes above the predetermined limit, the controller 217 will adjust the duty cycle of the RF energy being applied to maintain the predetermine temperature limit (step 516), e.g., lower the duty cycle. If the temperature at the tip 204 goes below the predetermined temperature limit, the duty cycle will be increased and, subsequently, the controller 217 will monitor the current output to ensure the current supplied is not greater than a predetermined current limit, e.g., 2 amps. If the current output is greater than the predetermined current limit, the duty cycle will be throttled back. Optionally, the predetermined temperature limit may be a range of temperatures of about 60° C. to about 99° C., and preferably a range of about 60° C. to about 80° C.

The controller 217 will also continuously measure impedance at the electrode (step 518). If the impedance is below a predetermined limit, e.g., 700 ohms, it will be determined that the electrode is still in contact with tissue and the controller 217 will then determine if the procedure timer associated with the selected channel has expired (step 522). If the procedure timer has not expired, the controller 217 will loop back to step 514 to control the power applied to the electrode to maintain the desired temperature. If the controller 217 determines the impedance is greater than the predetermined limit, it will be determined that the electrode is completely withdrawn and the controller 217 will stop applying power to the selected electrode (step 520). Once the electrode is completely withdrawn, the clinician will select the next channel and repeat the process until all electrode are withdrawn from the organ OR. However, if the impedance does not exceed the predetermined limit within the allowable procedure time as determined at step 522, the controller 217 will terminate the cauterization procedure and stop applying power to the selected channel.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A system for heat ablation of tissue in a patient comprising:
    a plurality of electrodes operatively connected to a source of radiofrequency energy and configured to apply RF energy to tissue at a patient site;
    a plurality of RF current restricting circuits, each circuit coupled between one of said plurality of electrodes and said source of radiofrequency energy, and configured to restrict RF energy to said electrode when said current restricting circuit is enabled and not restrict RF energy to flow to said electrode when said current restricting circuit is disabled;
    at least one return electrode adapted to contact the patient and configured to return RF energy to the RF source; and
    a switching mechanism configured to selectively enable each of said plurality of RF current restricting circuits, in one of a sequential and non sequential fashion, wherein said switching mechanism is isolated from each of said current restricting circuits.

2. The system as in claim 1, wherein the switch mechanism comprises a corresponding plurality of optical switching devices.

3. The system as in claim 1 wherein at least one of the current restricting circuits include:
    a switch configured to direct the flow of RF energy;
    a plurality of current restrictive devices arranged to restrict RF energy when said switch is disposed in a first position and not restrict RF energy when said switch is disposed in a second position;
    wherein said switching mechanism is optically coupled to said switch; and
    wherein said switching mechanism selects between said first position and said second position of said switch.

4. The system as in claim 3, wherein said plurality of current restrictive devices is a diode.

5. The system as in claim 4 wherein a plurality of diodes is arranged in an H-Bridge arrangement including a switch disposed therein wherein RF energy is conducted when said switch is closed.

6. The system as in claim 5 wherein the switch is a transistor.

7. A system for heat ablation of tissue in a patient comprising:
    a plurality of electrodes operatively connected to a source of radiofrequency energy and configured to apply RF energy to tissue at a patient site, wherein each electrode is individually discretely placeable in a patient;
    a plurality of RF current restricting circuits, each circuit coupled between one of said plurality of electrodes and said source of radiofrequency energy, and configured to restrict RF energy to said electrode when said current restricting circuit is enabled and not restrict RF energy to flow to said electrode when said current restricting circuit is disabled;
    at least one return electrode adapted to contact the patient and configured to return RF energy to the RF source; and
    a switching mechanism configured to selectively enable each of said plurality of RF current restricting circuits, in one of a sequential and non sequential fashion, wherein said switching mechanism is isolated from each of said current restricting circuits.

8. The system as in claim 7, wherein the switch mechanism comprises a corresponding plurality of optical switching devices.

9. The system as in claim 7, wherein at least one of the current restricting circuits include:
    a switch configured to direct the flow of RF energy;

a plurality of current restrictive devices arranged to restrict RF energy when said switch is disposed in a first position and not restrict RF energy when said switch is disposed in a second position;

wherein said switching mechanism is optically coupled to said switch; and wherein said switching mechanism selects between said first position and said second position of said switch.

10. The system as in claim 9, wherein said plurality of current restrictive devices is a diode.

11. The system as in claim 10, wherein a plurality of diodes is arranged in an H-Bridge arrangement including a switch disposed therein wherein RF energy is conducted when said switch is closed.

12. The system as in claim 11, wherein the switch is a transistor.

13. A system for heat ablation of tissue in a patient comprising:

a plurality of electrodes operatively connected to a source of radiofrequency energy and configured to apply RF energy to tissue at a patient site;

a plurality of RF current restricting circuits, each circuit coupled between one of said plurality of electrodes and said source of radiofrequency energy, and configured to restrict RF energy to said electrode when said current restricting circuit is enabled and not restrict RF energy to flow to said electrode when said current restricting circuit is disabled;

at least one return electrode adapted to contact the patient and configured to return RF energy to the RF source; and a dynamic switching mechanism configured to selectively enable each of said plurality of RF current restricting circuits, in one of a sequential and non sequential fashion, wherein said switching mechanism is isolated from each of said current restricting circuits.

14. The system as in claim 13, wherein the switch mechanism comprises a corresponding plurality of optical switching devices.

15. The system as in claim 13, wherein at least one of the current restricting circuits include:

a switch configured to direct the flow of RF energy;

a plurality of current restrictive devices arranged to restrict RF energy when said switch is disposed in a first position and not restrict RF energy when said switch is disposed in a second position;

wherein said switching mechanism is optically coupled to said switch; and wherein said switching mechanism selects between said first position and said second position of said switch.

16. The system as in claim 15, wherein said plurality of current restrictive devices is a diode.

17. The system as in claim 16, wherein a plurality of diodes is arranged in an H-Bridge arrangement including a switch disposed therein wherein RF energy is conducted when said switch is closed.

18. The system as in claim 17, wherein the switch is a transistor.

* * * * *